United States Patent [19]

Kingler et al.

[11] 4,191,777
[45] Mar. 4, 1980

[54] MALEIC ACID HALFAMIDES HAVING BLOOD PRESSURE RAISING ACTIVITY

[75] Inventors: Karl H. Kingler, Lagen; Klause Thiemer, Hanau; Fritz Stroman, Offenbach, all of Fed. Rep. of Germany

[73] Assignee: Deutsche Gold- und Silber-Scheideanstalt vormals Roessler, Frankfurt, Fed. Rep. of Germany

[21] Appl. No.: 969,068

[22] Filed: Dec. 13, 1978

[30] Foreign Application Priority Data

Dec. 16, 1977 [GB] United Kingdom ............... 52422/77

[51] Int. Cl.$^2$ .................. A61K 31/19; A61K 31/205; C07C 101/20
[52] U.S. Cl. ............................. 424/316; 260/340.5 R; 260/501.11; 424/319; 424/282; 562/401; 562/444
[58] Field of Search ............... 562/401, 444; 260/340.5 R, 501.11; 424/282, 316, 319, 282

[56] References Cited

U.S. PATENT DOCUMENTS

| 2,275,809 | 3/1942 | Roberts | 260/501.11 |
| 3,222,395 | 12/1965 | Schultz et al. | 562/444 |
| 3,576,854 | 4/1971 | Felder et al. | 562/401 |
| 4,002,666 | 1/1977 | Shirai et al. | 562/444 |

FOREIGN PATENT DOCUMENTS 901438 7/1962 United Kingdom .
1137596 12/1968 United Kingdom .

Primary Examiner—Bernard Helfin
Assistant Examiner—Vera C. Clarke
Attorney, Agent, or Firm—Cushman, Darby & Cushman

[57] ABSTRACT

There are prepare half amides (semi-amides) of unsaturated aliphatic dicarboxylic acids of the formula:

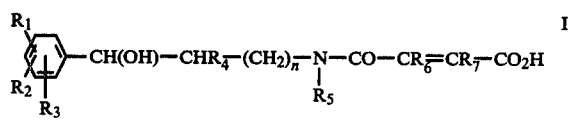

where $R_1$, $R_2$ and $R_3$ are the same or different and are hydrogen, halogen, a hydroxy group, a methyl group or a methoxy group or two of these together are a methylenedioxy group, $R_4$ is hydrogen or a methyl group, $R_5$, $R_6$ and $R_7$ independently are hydrogen or $C_1$–$C_4$ alkyl groups and n is 0 or 1 and their salts with the proviso that in the case of the free acids N[2-(3-hydroxyphenyl)-2-hydroxyethyl]-maleic acid monoamide is excluded. The compounds have blood pressure raising activity and also have antidepressive activity.

37 Claims, No Drawings

MALEIC ACID HALFAMIDES HAVING BLOOD PRESSURE RAISING ACTIVITY

BACKGROUND OF THE INVENTION

In British Pat. No. 1,137,596 in Example 6 there is described N-[2-(3-hydroxyphenyl)-2-hydroxyethyl]-maleic acid monoamide of the formula

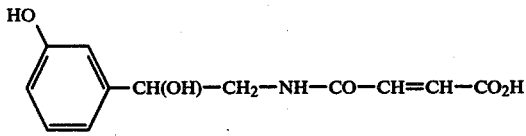

In British Pat. No. 1,137,596 there is described as pharmacological activity for such compounds an action of the blood circulation, particularly a favorable action at low pressure. In British Pat. No. 1,137,596 there is given as pharmacological activity for such compounds an effect on the blood circulation, particularly a favorable effect at low blood pressure.

Furthermore it is stated in British Pat. No. 901,438 that there are prepared maleic acid monoamide derivatives of the general formula

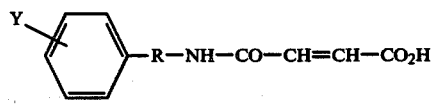

where Y is hydrogen, a halogen atom, a $C_1$–$C_{10}$ alkyl group or a $C_1$–$C_{10}$ alkyl group and R is an ethylene or propylene group, which, among others, also can be substituted by a $C_1$–$C_{10}$ alkyl residue and/or hydroxy group, which counteracts the separation of penicillin in the organisms. Several compounds also are supposed to be effective against gout and in a given case lower the cholesterol content in the blood. The only hydroxyalkyl compound specifically disclosed is N-(2,2-diphenyl-2-hydroxyethyl)-maleamic acid in Example 29.

SUMMARY OF THE INVENTION

According to the invention there are prepared half amides (semi-amides) of unsaturated aliphatic decarboxylic acids of the formula

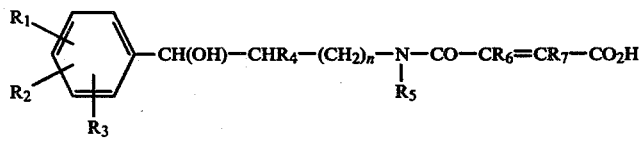

where $R_1$, $R_2$ and $R_3$ are the same or different and are hydrogen, halogen, a hydroxy group, a methyl group or a methoxy group or two of these together are a methylenedioxy group, $R_4$ is hydrogen or a methyl group, $R_5$, $R_6$ and $R_7$ independently are hydrogen or $C_1$–$C_4$ alkyl groups and n is 0 or 1 and their salts with the proviso that in the case of the free acids N-[2-(3-hydroxyphenyl)-2-hydroxyethyl]-maleic acid monoamide is excluded.

In the case where the groups $R_1$, $R_2$ and $R_3$ are halogen atoms they are fluorine, chlorine or bromine, particularly chloride. In case the groups $R_5$, $R_6$ and $R_7$ are alkyl groups they are especially methyl or ethyl groups.

In addition to the specific monoamides prepared in the working examples illustrative of other monoamides within the invention are N-[3-phenyl-3-hydroxyethyl] maleic acid monoamide, N-(2-phenyl-2-hydroxyethyl) maleic acid monoamide, N-(3-p-chlorophenyl-3-hydroxypropyl) maleic acid monoamide, N-(1-methyl-2-p-chlorophenyl-2-hydroxyethyl) maleic acid monoamide, N-(1-methyl-2-o-chlorophenyl-2-hydroxyethyl) maleic acid monoamide, N-(1-methyl-2-m-chlorophenyl-2-hydroxyethyl) maleic acid monoamide, N-(1-methyl-2-p-bromophenyl-2-hydroxyethyl) maleic acid monoamide, N-(1-methyl-2-p-fluorophenyl-2-hydroxyethyl) maleic acid monoamide, N-(1-methyl-2-o,p-dichlorophenyl-2-hydroxyethyl) maleic acid monoamide, N-(1-methyl-2-p-methylphenyl-2-hydroxyethyl) maleic acid monoamide, N-(2-p-methylphenyl-2-hydroxyethyl) maleic acid monoamide, N-(1-methyl-2-o-methylphenyl-2-hydroxyethyl) maleic acid monoamide, N-(1-methyl-2-m-methylphenyl-2-hydroxyethyl) maleic acid monoamide, N-(1-methyl-2-o,p-dimethylphenyl-2-hydroxyethyl) maleic acid monoamide, N-(1-methyl-2-2',4',6'-trimethylphenyl-2-hydroxyethyl) maleic acid monoamide, N-(1-methyl-2-p-methoxyphenyl)-2-hydroxyethyl) maleic acid monoamide, N-(2-o-methoxyphenyl)-2-hydroxyethyl) maleic acid monoamide, N-(1-methyl-2',3'-methylenedioxyphenyl)-2-hydroxyethyl) maleic acid monoamide, N-(1-methyl-3',4'-methylenedioxyphenyl)-2-hydroxyethyl) maleic acid monoamide, N-methyl-N-(1-methyl-2-phenyl-2-hydroxyethyl) maleic acid monoamide, N-(1-methyl-2-o,p-dihydroxyphenyl-2-hydroxyethyl) maleic acid monoamide, N-(1-methyl-2-phenyl-2-hydroxyethyl) ethyl maleic acid monoamide, N-(1-methyl-2-phenyl-2-hydroxyethyl) butyl maleic acid monoamide, N-(1-methyl-2-phenyl-2-hydroxyethyl) dimethyl maleic acid monoamide, N-(1-methyl-2-phenyl-2-hydroxyethyl)-diethyl maleic acid monoamide, N-(2-methyl-3-phenyl-3-hydroxypropyl) maleic acid monoamide.

The compounds of the invention are pharmacodynamically active and for example have an antidepressive action. Furthermore there have been observed with the salts of the compounds with phenylalkylamines, particularly with norephedrine, p-hydroxynorephedrine and other norephedrine derivatives surprisingly long maintaining of circulatory activities (as for example raising the blood pressure and positive inotropic effects) as well as an increase of the renal blood flow and a diuretic activity.

As salts there can be used physiologically (or pharmaceutically) compatible salts with metals such as K, Na, Li, Mg, Ca, or $NH_3$ or with amines or organic compounds which contain one or more basic nitrogen atoms.

Examples of such amines or basic organic compounds are (a) primary, secondary or tertiary alkyl amines with alkyl groups of 1–6 carbon atoms (e.g. triethylamine, diethylamine, ethylamine, trimethylamine, tributyl-amine, dibutylamine, isopropylamine, hexylamine, trihexylamine), $C_2$-$C_6$-alkylenediamines (e.g. ethylenediamine, propylene diamine, trimethylenediamine, hexamethylene diamine), primary, secondary or tertiary alkanolaimnes with alkylene residues of 2-6 carbon atoms (e.g. ethanolamine, diethanolamine, triethanolamine, isopropanolamine, diiospropanolamine, butanolamine, hexanolamine.

(b) $\beta$-phenyl-$C_1$-$C_4$-alkylamines and $\beta$-phenyl-$C_1$-$C_4$-alkanolamines wherein the phenyl group can be substituted for example by $C_1$-$C_5$ alkyl groups, $C_1$-$C_5$-alkoxy groups, hydroxy groups, hydroxymethyl groups or halogen atoms (F, Cl, Br) and whose amino groups also can be substituted by $C_1$-$C_6$-alkyl groups, phenyl-$C_1$-$C_4$ alkyl groups (which also can contain in the phenyl nucleus $C_1$-$C_5$ alkoxy groups or hydroxy groups) or $C_1$-$C_5$ alkyl or $C_2$-$C_5$ alkenyl groups which are substituted by a heterocyclic group (for example thienyl or pyridyl) and besides also can contain in the alkyl or alkenyl portion an oxo group or a hydroxy group. Examples are norephedrine, amphetamine, o, p or m-hydroxynorephedrine (i.e. 2-amino-1-(2' or 4' or 3'-hydroxy)phenyl-1-propanol), 3,4-dihydroxy or 3,5-dihydroxy norephedrine, (i.e. 2-amino-1-3',4'-dihydroxy) phenyl-1-propanol or 2-amino-1(3',5'-dihydroxy)phenyl-1-propanol), $\beta$-(2-hydroxy-1-methyl-phenethylamino)-3-methoxypropiophenone as well as ephedrine, 2-amino-1-phenylbutane, 1-amino-2-phenylethane, 2-amino-1-(4'-chloro) phenyl-1-propanol, 2-amino-1-(2'-chloro)phenyl-1-propanol, 2-amino-1-p-tolyl-1-propanol, (c) diphenyl-$C_2$-$C_6$ alkylamines whose amino group is substituted by straight or branched chain $C_1$-$C_5$ alkyl groups or phenyl $C_1$-$C_4$-alkyl groups (e.g. phenethyl group, phenylisopropyl group). Examples of these are N-(1-methyl-phenethyl) 3,3-diphenylpropylamine, 2,2-diphenyl ethylamine, 3,3-diphenylpropylamine, (d) 1-aryloxy-propanol-2-amines, e.g. phenoxypropanol-2-amine, ∂-naphthoxypropanol-2-amine, o-alkyloxyphenoxypropanol-2-amine, 1-aryloxy-propanol-(2)-amine whose amino group can be substituted by $C_1$-$C_6$ alkyl groups, phenyl-$C_1$-$C_4$ alkyl groups (e.g. the phenethyl group, phenyisopropyl group) or $C_2$-$C_6$ alkyl groups substituted by heterocyclic (e.g. by a pyridyl, thienyl or theophyllinyl or theobrominyl group) and whose aryl residue (which also can be substituted) is a phenyl, naphthyl or tetrahydronaphthyl residue or a mono-, di- or tricyclic heteroaromatic ring system (examples are set forth under (f)). Especially the aryl residue is an α-naphthyl group, a phenyl group, an o-allyoxyphenyl group, an indolyl-(4)- group, a 2-methylindolyl-(4)- group or a 2,3-dimethylindolyl-(4) group, (e) alkaloids with one or more basic nitrogen atoms, as for example atropine, hyoscyamine, scopolamine, codeine, ajmaline, spartein, (f) Basic substituted xanthine derivative, particularly theophylline and theobromine derivatives of the general formula

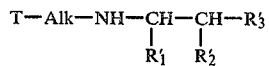

where T is a dialkylxanthinyl group, Alk is a straight or branched chain $C_2$-$C_6$ alkylene group, $R_1'$ is a hydrogen or a $C_1$-$C_4$ alkyl group (e.g. methyl, ethyl, isopropyl, butyl), $R_2'$ is hydrogen or a hydroxy group and $R_3'$ is a $C_1$-$C_5$ alkyl group (particularly once or twice), $C_1$-$C_5$-alkoxy groups, hydroxymethyl groups or the methylenedioxy substituted phenyl group or an aryloxymethyl group wherein as aryl groups there can be the naphthyl group, the tetrahydronaphthyl group or a mono-, di-, or tricyclic heteroaromatic ring system which in a given case also can be substituted once to three times by lower alkyl, alkoxy, alkenyl or alkenyloxy group or through halogen atoms (e.g. chlorine, bromine, fluorine). Examples of the heteroaromatic ring systems are indole, isoindole, benzimidazole, quinoline, dihydroquinoline, tetrahydroquinoline, isoquinoline, pyrazole, thiazole, methylindole, methylisoindole, methylbenzimidazole, methylquinoline, methyldihydroquinoline, methyltetrahydroquinoline, methylisoquinoline, methylpyrazole, methylthiazole, dimethylindole, dimethylquinoline, dimethylisoquinoline, dimethylbenzimidazole, (the methyl group or groups are located in the bicyclic residues preferably in the ring which contains the heteroatom).

Those salts in which the basic component has formula II

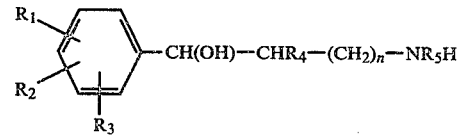

wherein the symbols $R_1$ to $R_5$ and n are as definded above have particularly favorable activities. Examples of such basic components are norephedrine, p-hydroxynorephedrine, m-hydroxynorephedrine, 3,4-dihydroxynorephedrine, noradrenaline, ephedrine and 3,4-dihydroxyephedrine.

The production of the compounds of the invention takes place by reaction of a compound of formula II with a compound of formula III.

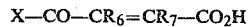

wherein $R_1$ through $R_7$ are as defined above and wherein any hydroxy group or carboxy group of compound III can also be protected and X is a halogen atom, (e.g. chlorine, bromine, or iodine) a $C_1$-$C_6$ alkoxy group (e.g. methoxy, ethoxy, butoxy or hexoxy), a cyanomethoxy group, a carboxymethoxy group or an aryloxy (e.g. phenoxy, naphthoxy, tolyloxy) or X with the free carboxy group forms a 5 membered acid anhydride ring.

The reaction between the compound of formula II and the compound of formula III can take place with or without a solvent at a temperature between 0° and 200° C., especially 15°-150° C. As solvents or suspension agents there can be used aromatic hydrocarbons such a benzene, toluene and xylene, aliphatic halohydrocarbon such as chloroform and methylene chloride, non-cyclic or cyclic ethers such as tetrahydrofurane, dioxane, diethyl ether and diisopropyl ether, alcohols such as ethanol, isopropanol, butanol and methanol, pyridine, tetramethyl urea, dimethyl formamide, dimethyl sulfoxide and N-methyl pyrrolidone.

Many times it is advantageous to use the reactant II in excess (particularly if case X is an alkoxy group). In a given case it is favorable to add a condensation agent such as dicyclohexylcarbodiimide, tetraethyl pyrophosphite, 5-(3'-sulfonyl-phenyl) ethyl isooxazole, sulfurous acid bis alkyl amides (for example SO[N(CH$_3$)$_2$]$_2$) or N,N$^1$-carboxyldiimidazole (in case X=OH) or to add basic materials (tertiary amines, e.g. triethyl amine or tributyl amine, alkali carbonates, e.g. sodium carbonate or potassium carbonate, alkali hydrogen carbonates, e.g. sodium bicarbonate, or potassium bicarbonate, alkali acetates, e.g. sodium acetate or potassium acetate, alkaline earth carbonates, e.g. calcium carbonate or magnesium carbonate, alkali hydroxide, e.g. sodium hydroxide or potassium hydroxide, etc. The amine component II can also be added in the form of an acid addition salt; in this case in most instances it is necessary to add acid binding basic material. In the case where X of compound III is a halogen atom it is Cl, Br or I, preferably Cl or Br. In the case where X of compound III is an aryloxy group, it is for example a phenoxy group wherein the phenyl residue can be substituted by a lower alkyl $C_1$–$C_6$ residue (e.g. methyl, ethyl, isopropyl, propyl, butyl or hexyl), lower alkoxy ($C_1$–$C_6$) (e.g. methoxy, ethoxy, propoxy, butoxy, hexoxy), halogen atoms (Cl, F, Br), nitro groups or cyanogroups.

Hydroxy groups present in the starting compounds II, particularly phenoltic hydroxy groups (in case $R_1$, $R_2$ and/or $R_3$=OH) as well as the carboxy group of the compound III can contain known and customary protective groups. It depends in this connection upon which groups are easily split off by hydrolysis and in a given case are already split off during the reaction. In case such protective groups are not split off in the reaction process then a splitting off takes place after the reaction. Frequently because of their method of protection, the starting compounds already contain this type of protective group.

These protective groups for example can be easily solvolytically splittable acyl groups. The solvolytically splittable protective group are split off for example by saponification with dilute acids (e.g. hydrochloric acid, phosphoric acid or sulfuric acid) or by means of basic material (potash, soda, aqueous alkali solutions (e.g. sodium methylate, sodium ethylate or potassium ethylate)), alcoholic alkali solution (e.g. alcoholic sodium hydroxide solution or alcoholic potassium hydroxide where the group is ethanol, or ammonia) at a temperature between 10° and 150° C., particularly 20°–100° C.

Examples of hydrolytically splittable groups are the trifluoroacetyl group, phthalyl group, trityl group, p-toluenesulfonyl group and similar groups as well as lower alkanoyl groups such as the acetyl group, formyl group, tert. butylcarboxy group and the like.

The production of the salts take place by bringing together the acid of formula I with the corresponding amine in a conventional solvent (lower aliphatic alcohol, (e.g. methyl alcohol, ethyl alcohol, isopropyl alcohol or butyl alcohol), a lower aliphatic ketone, e.g. acetone or methyl ethyl ketone, ester of a lower aliphatic acid with a lower alcohol, e.g. methyl acetate, ethyl acetate, propyl acetate, butyl acetate, methyl formate, ethyl formate, methyl propionate, or ethyl propionate at a temperature between 15° and 100° C., especially 20°–60° C.

Generally the components are used in equivalent amounts. In the case of the metal salts as the basic component there is used for example corresponding metal hydroxide or metal carbonate.

For the splitting of a racemate there can be reacted with each other either equivalent or nonequivalent amounts of the optically active half amide (0.4–1.2 moles, preferably 0.5–1.0 mole, of half amide per mole of base) and base in a solvent at a temperature between 0°–100° C., for example 10°–40° C., preferably 15°–30° C. The reaction can take place with or without stirring. In a given case slow cooling during the crystallization is suitable. Innoculation with the previously produced desired diastereoisomeric salt from pure components can be recommended. As in other racemate splitting processes the solvents or mixtures of solvents which can be used are variable in a wide range. Examples of solvents are alcohols such as methanol, ethanol, isopropanol and butanol; ketones such as acetone, methyl, ethyl ketone and methyl isobutyl ketone; esters such as ethyl acetate and butyl acetate, amides such as dimethyl formamide and dimethyl acetamide; ethers such as diethyl ether and dioxane; water, particularly in admixture with organic solvents (e.g. acetone, ethanol).

The amount of solvent based on the sum of the amounts of acid and base added generally is between twice and twenty fold; the preferred range is about three to eight fold.

The amines for the reaction with the half amides in a given case can also be added as the corresponding salt with an acid, preferably a weak acid (an example of the salt would be the acetate). In a given case in such case the half amide (amidcarboxylic acid) is added as the metal salt (for example the alkali metal salt, e.g., the sodium or potassium salt).

As a rule in the reaction of the half amide I with the case one diastereomer precipitates out directly while the other remains in solution. However, in the event that in one or the other case the precipitating diastereomeric form is strongly contaminated by the other form, then the production of the pure form takes place in the customary manner through fractional crystallization.

The diastereomer obtained can be decomposed in an easy manner using alkali (for example alkali metal hydroxide such as sodium or potassium hydroxide), ammonia or a mineral acid such as hydrochloric acid or sulfuric acid. The difficulty soluble diastereomer is treated for example with the alkali (preferably $NH_3$ or NaOH) and, in case the base does not precipitate, extracted with a solvent that is incompatible or immiscible with water such a chloroform, methylene, chloride, benzene or ether, whereby the optically active form can be isolated in greater purity from the organic phase. The mother liquor, from which the difficulty soluble diastereomer is separated is generally distilled off and the residue taken up in a solvent in which the residual (±) base separates as insoluble (for example, aromatic hydrocarbons such as toluene, xylene, benzene). After several hours the (±) base is separated off and the filtrate evaporated, whereby the other antipode remains behind.

The aqueous phase from which the optically active base was extracted is then acidified with a mineral acid (HCl, $H_2SO_4$), whereupon the amidoacid precipitates, the thus recovered amidoacid for the most part can again be added for the splitting of the racemate without further purification.

If the salts obtained in the splitting of the racemate are decomposed with acids (e.g. mineral acids such as HCl, $H_2SO_4$) then the amidoacid precipitates out first. The filtrate is either, or after concentration made, alkaline and the optically active base extracted by a solvent (lower aliphatic halohydrocarbons such as chloroform or lower aliphatic dialkyl ethers such as diethyl ether).

Immediately below there is described by way of example the splitting of the racemate of (±)-p-hydroxynorephedrine, (page 28 of handwritten) which crystallized out was removed with suction and boiled with 550 ml of isopropanol for purification. After cooling it was filtered off with suction and dried in a vacuum at 60° C. Yield: 99.3 grams=75.7% of theory M.P. 163°–165° C., $[\alpha]_D^{20}$ (1% in absolute ethanol): +4.1°.

RECOVERY OF (−)-P-HYDROXYNOREPHEDRINE 94 grams of this salt were stirred at room temperature for about 1 hour with 96 ml of 2 N NaOH. It was placed overnight in the refrigerator, filtered off with suction, subsequently washed with a little water and dried at 40° C. in a vacuum.

Yield: 72.0%. M.P. 162°–166° C. $[\alpha]_D^{20}$ (2% in absolute ethanol): −17.5°. $[\alpha]_D^{20}$ (3.5% in 1 N Hcl): −40.7°.

RECOVERY OF (+)-P-HYDROXYNOREPHEDRINE

The ethanolic filtrate from the splitting of the racemate was evaporated in a vaccum and the residue recrystallized from isopropanol. There were obtained 127.5 grams of crude (−) NEMA salt of (+)-p-hydroxynorephedrine. By stirring up with 152 ml of 2 N NaOH and subsequently standing for twelve hours in the refrigerator the (+) base separated out. It was filtered off with suction and recrystallized from isopropanol.

Yield: 60.4%, M.P. 163°–166° C. $[\alpha]_D^{20}$ (2% in absolute ethanol): +17.35°.

The salts of the final materials can be again converted in known manner into the compounds of formula I, for example using strong acids (for example with inorganic mineral acids, e.g. hydrochloric acid or sulfuric acid) or ion exchangers (e.g. strong cation exchange resins such as sulfonated styrene-divinyl benzene cation exchange resins).

Within the scope of the present invention there are also included within the compounds of general formula (I) the possible stereoisomers and optically active compounds and mixtures thereof, especially the racemate. Mixtures of diastereoisomers can be separated in known manner, for example through fractional crystallization. Optically active compounds can be obtained according to customary methods, for example by recrystallization of salts of the racemic acids of formula (I) with optically active bases or in a given case by use of optically active starting materials in the synthesis. Also the organic basic compounds used for the salt formation can be present as pure optically active forms, as racemates or as diastereomers.

Illustrative of additional bases are 3',5'-dihydroxynorephedrine and 2'-hydroxynorephedrine.

The compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared with the usual pharmaceutical excipients, assistants, carriers and diluents.

As carriers and assistants, for example, are those recommended in the following literature as adjuvants for pharmacy, cosmetic and related fields such as Ullmann's Encyklopadie der technischer Chemie, Vol. 4 (1953), pages 1 to 39' Journal of Pharmaceutical Sciences 52 (1963), pages 918 et seq.; H. V. Czetsch-Lindenwald, Hilfsstoffe fur Pharmazie und angrenzende Gebiete; Phar Ind. 2 (1961) pages 72 et seq.; Dr. H. P. Fiedler, Lexicon der Hilfsstoffe fur Pharmazie, Kosmetik und angrenzende Begiete, Cantor Kg. Aulendorf i. Wurtt (1971).

Examples of such materials include gelatin, natural sugars such as sucrose or lactose, lecithin, pectin, starch (for example cornstarch), alginic acid, tylose (methyl cellulose), talc, lycopodium, silica (for example colloidal silica), glucose, cellulose, hydroxyethyl cellulose), stearates, e.g., methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example peanut oil, castor oil, olive oil, sesame oil, cottonseed oil, corn oil, wheat germ oil, sunflower seed oil, cod-liver oil), mono-, di- and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate, pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols) or polyhydric alcohols such as glycols, glycerine, diethylene glycol, pentaerythritol, sorbitol, mannitol, ethyl, alcohol, butyl alcohol, octadecyl alcohol, etc. e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivates, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g. monoacetic, diacetin, glyceryl monostearate, glyceryl distearate, glyceryl monopalmitate, paraffins and the like.

In the production of the preparation there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191–195).

Furthermore, there can be added preservatives, stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium meta bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatices there can be used for example sorbic acid, p-hydroxybenzoic acid esters (for example, lower alkyl esters such as the methyl ester and the ethyl ester), benzoic acid, sodium benzoate, trichloroisobutyl alcohol, phenol, cresol, benzethonium chloride and formalin derivatives.

The pharmacological and galenical treatment of the compounds of the invention takes place according to the usual standard methods. For example, the active material or materials and assistants or carriers are well mixed by stirring or homogenization (for example, by means of a colloid mill or ball mill), wherein the operation is generally carried out at temperatures between 20° and 80° C., preferably 20° to 50° C.

The application of active material or drug can take place on the skin or muccous membrane or internally, for example, orally, enterally, pulmonarily, rectally, nasally, vaginally, lingually, intravenously, intraarterially, intracardially, intramuscularly, intraperitoneally, intracutaneously or subcutaneously.

The addition of other medicines is also possible.

The compounds of the invention show circulatory stimulating activity, especially blood pressure increasing activity, on narcotized animals in electronic measurement of blood pressure, contractility and heart time volumes.

The measurements of the blood pressure takes place in the customary manner with electronic pressure absorbers (stathaem) directly (sanguinary). The contractility (dp/dt max) is ascertained from the pressure of the left heart ventricle (method of Schaper et al., Archiv Kreislaufforsch, Vol. 46, 27(1965). The heart time volume was determined according to the cold dilution method (according to W. F. Hamilton et al, Amer. J. Physiol, Vol. 99, 543 (1932) with the help of a fixed programmed analog calculator (method of H. Slama and J. Piiper, Kreislaufforschung, Vol. 53 page 322 (1964).

For example in the above mentioned test methods at a dosage of 1 mg/kg body weight dog the average arterial middle pressure is increased about 20% and the heart time volume 100%. The contractility (speed of increase in pressure) is increased about 70%.

This circulatory stimulating activity is comparable to the known medicine, norephedrine.

The lowest effective dosage for increasing blood pressure in the above mentioned animal test for example is 0.3 mg/kg orally, 0.1 mg/kg intravenously. As the general dosage range for the above mentioned blood pressure increasing activity animal test as above there can be used for example 1 to 10 mg/kg orally, especially 3 mg, 0.1 to 1 mg.kg intravenously, especially 0.3 mg/kg.

The compounds of the invention are indicated for use in heart circulatory failure, shock conditioned disturbances, hypotoni, orthostatic disturbances, collapse. The pharmaceutical preparations generally contain between 1 to 50 mg of the active component or components of the invention.

The compounds can be delivered in the form of tablets, capsules, pills, dragees, plugs, aerosols or in liquid form. As liquid forms there can be used for example oily or alcoholic or aqueous solutions as well as suspensions and emulsions. The preferred forms of use are tablets which contain between 1 and 50 mg or solutions which contain between 0.5 and 5% of active material.

In the individual doses the amount of active component of the invention can be used for example in an amount of:

a. in oral dispensation between 5 and 40 mg;

b. in parenteral dispensation (for example intravenously, intramuscularly) between 1 and 20 mg.

c. in medicinal forms for inhalation (solutions or aerosols) between 1 and 5 mg.

d. in dispensation rectally or vaginally between 5 and 30 mg. (The dosages are always based on the free base.)

For example, there is recommended the use of 1 to 3 tablets containing 5 to 40 mg of active ingredients 3 times daily or for example, intravenously the injection 1 to 6 times daily of an 1 to 10 ml ampoule containing 1 to 20 mg of active substance. In oral preparations the minimum daily dosage for example is 10 mg; the maximum daily dosage in oral administration should not be over 120 mg.

In venerinary medicine the compounds of the invention can be used in treating dogs, cats, horses and cows. The individual dosages in treating dogs, cats, horses and cows in general orally are between approximately 1 and 20 mg/kg body weight; the parenteral dosage approximately between 0.1 and 3 mg/kg body weight.

The drugs can be used in human medicine, in veterinary medicine as well as in agriculture alone or in admixture with other pharmacologically active materials.

Unless otherwise indicated all parts and percentages are by weight.

The compositions can comprise, consist essentially of or consist of the materials set forth.

The methods can comprise, consist essentially of or consist of the steps set forth with the materials shown.

The free acids of formula I besides are valuable racemate splitting agents for racemic bases and therefore are particularly significant for the production of optically active pharmaceutical materials. This use is disclosed and claimed in companion Klingler et al application Ser. No. 969,067 filed on even date and entitled "Process For the Production of Optically Active Bases"

(based on British application 52421/77). The entire disclosure of the copending Klinger et al application is hereby incorporated by reference and relied upon.

DESCRIPTION OF THE PREFERRED EMBODIMENTS

EXAMPLE 1

(+)-Ψ-N-(1-Methyl-2-phenyl-2-hydroxyethyl)-maleic acid monoamide (abbreviation: (+)-Ψ-NEMA).

165.4 grams of maleic anhydride were dissolved in 1250 ml of warm toluene. To this there were quickly dropped in with stirring a 50° C. warm solution of 255 grams of (−)-Ψ-norephedrine in 1250 ml of toluene and the mixture stirred subsequently for another hour at 80° C. internal temperature. Subsequently the mixture was allowed to cool to room temperature, the amide acid which crystallized out filtered off with suction and dried at 60° C. in a vacuum.

Yield: 419.9 grams (99.9% of theory).

After recrystallization the reaction product melted at 152°–155° C. $[\alpha]_D^{20}$ (2.5% in 96% ethanol). 17.64°

(−)-Norephedrine Salt 25 grams of (−)-norephedrine and 41.2 grams of (+)-Ψ-NEMA were dissolved hot in 200 ml of acetone. Upon cooling the salt crystallized out.

Yield: 64.5 grams=97.6% of theory. M.P. 149°–151° C. $[\alpha]_D^{20}$ (2.5% in ethanol): −64.4°

EXAMPLE 2

(−)-N-(methyl-2-phenyl-2-hydroxyethyl)-maleic acid monoamide (abbreviation (−)-NEMA)

16.3 grams of maleic anhydrice were dissolved in 300 ml of toluene. There were dropped into this solution with stirring a 50° C. warm solution of 25.0 grams of (−)-norephedrine in 50 ml of toluene. The mixture was stirred a further hour at this temperature, allowed to cool and filtered off with suction. It can be recrystallized from ethyl acetate for purification.

Yield: 32.6 grams=79% of theory M.P. 155°–158° C. $[\alpha]_D^{20}$ (5% in ethanol): −7.69°

(−)-Ephedrine Salt 20.6 grams of (−)-ephedrine and 31 grams of (−)-NEMA were dissolved in 155 ml of acetone. The mixture was treated with dry ether until there occurred a permanent turbidity. The mixture was allowed to stand at room temperature for several days, then filtered off with suction and dried in a vacuum Yield: 37.5 grams=73% of theory, M.P. 118°–122° C. $[\alpha]_D^{20}$ (1% in 96% ethanol) −39.5°

(−)-Norephedrine Salt 25 grams of (−)-norephedrine and 41.2 grams of (−)-NEMA were dissolved hot in 200 ml of acetone. The mixture was allowed to cool and the crystalline salt filtered off with suction.

Yield: 56.3 grams=85% of theory. M.P. 142°–144° C. $[\alpha]_D^{20}$ (1% in ethanol: 7.39°

(−)-Ψ-Norephedrine Salt 34.5 grams of (−)-Ψ-norephedrine and 57 grams of (−)-NEMA were dissolved hot in 460 ml of ethyl acetate. After the cooling to room temperature the product was filtered off with suction and dried.

Yield: 90.5 grams=98.4% of theory M.P. 153°–155° C. $[\alpha]_D^{20}$ (1% in ethanol): 7.70°

(−)-p-Hydroxynorephedrine Salt 10 grams of (−)-p-hydroxynorephedrine and 14.9 grams of (−)-NEMA were stirred for two hours in 125 ml of isopropanol. The mixture was allowed to stand for 15 hours at 20° C., the product filtered off with suction and dried at 50° C. in a vacuum.

Yield: 23.5 grams=94.4% of theory. M.P. 162°–164°. $[\alpha]_D^{20}$ (1% in ethanol): +3.8°

This salt can also be obtained from racemic p-hydroxynorephedrine utilizing the racemate splitting properties of the maleic acid amide (maleamic acid) of Example 2.

A mixture of 100 grams of (±)-p-hydroxynorephedrine, 149 grams of (−)-NEMA and 1.25 liters of absolute ethyl alcohol were stirred for 8 hours at 20° C. and allowed to stand a further 16 hours. Then there was filtered off with suction the (−)-NEMA salt of the (−)-p-hydroxynorephedrine which crystallized out and for purification it was boiled up with 550 ml of isopropanol. After the cooling it was filtered off with suction and dried in a vacuum at 60° C.

Yield: 94.3 grams=75.7% of theory M.P. 163°–165° C. $[\alpha]_D^{20}$ (1% in absolute ethanol): +4.1°

EXAMPLE 3

(−)-Ψ-N-(1-Methyl-2-phenyl-2-hydroxy-ethyl)-methyl-maleic acid-monoamide.

A mixture of 14 grams of citraconic anhydride and 18.9 grams of (−)-Ψ-norephedrine were stirred in 180 ml of dimethyl formamide for five hours at 40°–50° C. The mixture was allowed to cool, treated with stirring with an additional 18.9 grams of (−)-norephedrine, the reaction solution obtained filtered and the solvent distilled off in a vacuum. The salt remaining behind was dissolved in cold water and after acidifying with hydrochloric acid stirred for 1 hour. The product was filtered off with suction, washed with water and dried in a vacuum at 60° C.

M.P. 137°–140° C. $[\alpha]_D^{20}$ (2.5% in 96% ethanol): −1.6°.

EXAMPLE 4

(+)-N-(1-Methyl-2-phenyl-2-hydroxyethyl)-maleic acid monoamide (abbreviation: (+)-NEMA)

32.6 grams of maleic anhydride were dissolved in 600 ml of toluene and there were dropped into this solution under stirring a 50° C. warm solution of 50.0 grams of (+)-norephedrine in 100 ml of toluene. Then stirring was continued for 30 more minutes at this temperature. The product was allowed to cool, filtered off with suction, dried and recrystallized from ethyl acetate. Yield: 63.5 grams=77.0% of theory. M.P. 154°–156°

$[\alpha]_D^{20}$ (5% in ethanol): +7.8°

(+)-Norephedrine Salt 50 grams of (+)-norephedrine and 82.4 grams of (+)-NEMA were dissolved warm in 400 ml of isopropanol. The mixture was filtered and allowed to cool down slowly to 5° C. The salt which crystallized out was filtered off with suction and dried in a vacuum at 60° C. Yield: 118.3 grams=89.5% of theory. M.P. 141°–143° C.

$[\alpha]_D^{20}$ (1% in ethanol): 7.40°.

(+)-Ψ-Norephedrine Salt 34.5 grams of (+)-Ψ-norephedrine and 57 grams of (+)-NEMA were dissolved hot in 460 ml of ethyl acetate. After cooling to room temperature the product was filtered off and dried. Yield: 90.5 grams=98.4% of theory. M.P. 153°–156° C.

$[\alpha]_D^{20}$ (1% in ethanol): $-7.70°$

EXAMPLE 5

(−)-N-(1-Methyl-2-p-hydroxyphenyl-2-hydroxy-ethyl) maleic acid monoamide (abbreviation: (−)-p-Hydroxy-NEMA)

50 grams of (−)-p-hydroxynorephedrine were stirred together with 29.3 grams of maleic anhydride in 100 ml of dimethyl formamide. After the dying away of a weak exothermic reaction the mixture was heated to 80° C., and held at this temperature for a further hour. The mixture was treated with 100 ml of water, stirred for a further hour, the product filtered off with suction on the next day and dried in a vacuum.

Yield: 76.1 grams=96% of theory. M.P. 146°–148° C.

It was subsequently stirred up with cold isopropanol for purification filtered off with suction and dried. M.P. 150°–152° C., $[\alpha]_D^{20}$ (2% in 96% ethanol): $-13.05°$

EXAMPLE 6

(−)-N-(1-Methyl-2-p-hydroxyphenyl-2-hydroxy-ethyl)-maleic acid monoamide (abbreviation: (−)-p-Hydroxy-NEMA)

100 grams of (+)-p-hydroxy-norephedrine were stirred with 60.8 grams of maleic anhydride in 150 ml of dimethyl formamide. After dying down of a weak exothermic reaction the mixture was heated to 80° C. and held for the further hour at this temperature. The mixture was treated with 100 ml of water, stirred for a further hour, the product filtered off with suction on the next day and dried in a vacuum.

Yield: 120 grams of pure (+)-p-hydroxy-NEMA M.P. 151°–153° C. $[\alpha]_D^{20}$ (2% in 96% ethanol): $+12.9°$ In place of dimethyl formamide there can also be used isopropanol as the solvent.

EXAMPLE 7

Tablet Formation 25 grams of the (−)-norephedrine salt of (−)-NEMA were mixed with 25 grams of corn starch and 60 grams of lactose. The powder was granulated with a solution of 2.5 grams of methyl hydroxypropyl cellulose in about 80 ml of 30% ethanol, the dried granulate mixed with 10.5 grams of corn starch, 9 grams of talc, 62.5 grams of microcrystalline cellulose and 0.5 gram of magnesium stearate and there pressed into tablets in known manner.

EXAMPLE 8

Injectable Solution 10 mg of the (−)-p-hydroxynorephedrine salt of (−)-NEMA were dissolved in 200 mg of propylene glycol and the solution filled up to 2.0 ml with double distilled water. The solution was filtered through a sterile filter and filled under aseptic conditions into ampoules.

What is claims is:

1. A half amide of an unsaturated aliphatic dicarboxylic acids of the formula:

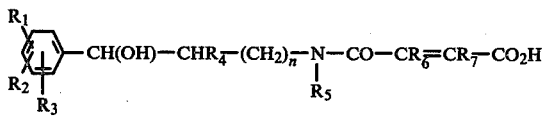

where $R_1$, $R_2$ and $R_3$ are the same or different and are hydrogen, halogen, a hydroxy group, a methyl group or a methoxy group or two of these together are a methylenedioxy group, $R_4$ is hydrogen or a methyl group, $R_5$, $R_6$ and $R_7$ independently are hydrogen or $C_1$–$C_4$ alkyl groups and n is 0 or 1, or a salt of a compound of formula I with a pharmaceutically acceptable metal, ammonia or a pharmaceutically acceptable organic basically reacting compound, with the proviso that when the compound of formula I is not in the salt form it is not N-[2-(3′-hydroxyphenyl)-2-hydroxyethyl]-maleic acid monoamide.

2. A compound according to claim 1 in the form of the free acid.

3. A compound according to claim 2 wherein $R_1$, $R_2$ and $R_3$ are hydrogen, halogen, methyl, or methoxy or two of $R_1$, $R_2$ and $R_3$ together are a methylenedioxy group.

4. A compound according to claim 3 where $R_1$, $R_2$ and $R_3$ are all hydrogen.

5. A compound according to claim 4 wherein $R_5$ is hydrogen one of $R_6$ and $R_7$ is hydrogen and the other of $R_6$ and $R_7$ is hydrogen or methyl.

6. A compound according to claim 5 wherein $R_4$ is methyl.

7. A compound according to claim 6 wherein n is 0.

8. A compound according to claim 2 wherein $R_1$ is a hydroxy group in the ortho or para position and $R_2$ and $R_3$ are hydrogen or hydroxy.

9. A compound according to claim 8 where $R_2$ and $R_3$ are both hydrogen.

10. A compound according to claim 8 where $R_2$ is hydrogen and $R_3$ is hydroxy.

11. A compound according to claim 1 in the form of a salt.

12. A compound according to claim 11 wherein $R_1$, $R_2$ and $R_3$ are hydrogen, halogen, methyl or methoxy or two of $R_1$, $R_2$ and $R_3$ together are a methylenedioxy group.

13. A compound according to claim 12 wherein $R_1$, $R_2$ and $R_3$ are all hydrogen.

14. A compound according to claim 13 wherein $R_5$ is hydrogen, one of $R_6$ and $R_7$ is hydrogen and the ofther of $R_6$ and $R_7$ is hydrogen or methyl.

15. A compound according to claim 14 wherein $R_4$ is methyl.

16. A compound according to claim 15 wherein n is 0.

17. A compound according to claim 11 wherein $R_1$ is a hydroxy group and $R_2$ and $R_3$ are hydrogen or hydroxy.

18. A compound according to claim 17 wherein $R_1$ is in the para or ortho position.

19. A compound according to claim 18 wherein $R_1$ is in the meta position.

20. A compound according to claim 17 wherein $R_2$ is hydrogen and $R_3$ is hydroxy.

21. A salt according to claim 11 wherein it is a salt with β-phenylethylamine or β-phenylethylamine which is substituted in the β position with a hydroxy group, in the α position with a methyl group or in the benzene ring with one or two hydroxy groups or on the nitrogen atom with a methyl group.

22. A salt according to claim 21 wherein $R_1$ is hydrogen and $R_2$ and $R_3$ are hydrogen or hydroxy.

23. A salt according to claim 22 wherein $R_2$ and $R_3$ are hydrogen.

24. A salt according to claim 22 wherein $R_2$ is hydrogen and $R_3$ is hydroxy.

25. A compound according to claim 22 wherein $R_1$ and $R_2$ are hydrogen and $R_3$ is hydroxy.

26. A compound according to claim 22 where $R_4$ is methyl, $R_5$ is hydrogen one of $R_6$ and $R_7$ is hydrogen and the other of $R_6$ and $R_7$ is hydrogen or methyl.

27. A compound according to claim 26 wherein the β-phenylethylamine has a methyl group in the α position.

28. A compound according to claim 27 wherein the β-phenylethylamine is norephedrine, pseudonorephedrine, ephedrine or p-hydroxynorephedrine.

29. A compound according to claim 28 wherein $R_6$ and $R_7$ are both hydrogen and $R_1$, $R_2$ and $R_3$ are hydrogen.

30. A compound according to claim 28 wherein $R_1$ and $R_2$ are hydrogen and $R_3$ is para-hydroxy.

31. A compound according to claim 27 wherein there is a hydroxy group in the β position of the phenylethylamine.

32. A compound according to claim 31 wherein the phenyl ring of the phenylethylamine has 1 to 2 hydroxy groups.

33. A compound according to claim 32 wherein the hydroxy groups are in the 2-position, the 4-position or the 3,5-position.

34. A composition comprising a compound of claim 21 with a pharmaceutically acceptable carrier, said compound being present in an amount to have a blood pressure increasing effect.

35. A composition comprising a compound of claim 1 with a pharmaceutically acceptable carrier, said compound being present in an amount to have a blood pressure increasing effect.

36. A process comprising administering to a mammal an amount of a compound according to claim 1 effective to increase the blood pressure of the mammal.

37. A process comprising administering to a mammal an amount of a compound according to claim 21 effective to increase the blood pressure of the mammal.

* * * * *